United States Patent [19]
Lange et al.

[11] Patent Number: 5,597,437
[45] Date of Patent: Jan. 28, 1997

[54] ZERO SCRAP ABSORBENT CORE FORMATION PROCESS

[75] Inventors: Stephen J. Lange, Cincinnati, Ohio; Douglas H. Benson, West Harrison, Ind.; John W. Hackett, Cincinnati, Ohio; Gary D. Lavon, Middletown, Ohio; Bret D. Seitz, West Chester, Ohio

[73] Assignee: Procter & Gamble, Cincinnati, Ohio

[21] Appl. No.: 371,886

[22] Filed: Jan. 12, 1995

[51] Int. Cl.$^6$ .............................. B32B 31/08; B32B 31/18
[52] U.S. Cl. ...................... 156/260; 156/259; 156/264; 156/269; 156/324; 604/385.1
[58] Field of Search .................... 156/259, 260, 156/264, 324, 269; 604/385.1

[56] References Cited

U.S. PATENT DOCUMENTS

| | | | |
|---|---|---|---|
| Re. 26,151 | 1/1967 | Duncan et al. | 128/284 |
| 1,424,005 | 7/1922 | Drury . | |
| 1,776,353 | 9/1930 | Dunbar et al. . | |
| 2,709,475 | 5/1955 | Steckel et al. | 154/1 |
| 3,072,123 | 1/1963 | Davis | 128/284 |
| 3,180,335 | 4/1965 | Duncan et al. | 128/287 |
| 3,488,788 | 1/1970 | Goujon et al. | 2/224 |
| 3,527,221 | 9/1970 | Croon | 128/287 |
| 3,559,648 | 2/1971 | Mason, Jr. | 128/287 |
| 3,566,752 | 3/1971 | Dreher | 93/1 |
| 3,636,951 | 1/1972 | Glasgow | 128/284 |
| 3,691,570 | 9/1972 | Gaines et al. | 5/347 |
| 3,699,966 | 10/1972 | Chapuis | 128/290 |
| 3,744,383 | 7/1973 | Finch et al. | 93/35 |
| 3,744,494 | 7/1973 | Marsan | 128/287 |
| 3,768,530 | 10/1973 | Coco | 144/318 |
| 3,776,233 | 12/1973 | Schaar | 128/287 |
| 3,860,003 | 1/1975 | Buell | 128/287 |
| 3,871,378 | 3/1975 | Duncan et al. | 128/290 |
| 3,875,837 | 4/1975 | Dussaud | 83/46 |
| 3,878,283 | 4/1975 | Jones, Sr. | 264/152 |
| 3,890,973 | 6/1975 | Davis et al. | 128/286 |
| 3,929,134 | 12/1975 | Karami | 128/284 |
| 4,029,101 | 6/1977 | Chesky et al. | 128/290 |

(List continued on next page.)

FOREIGN PATENT DOCUMENTS

| | | |
|---|---|---|
| 0539032 | 4/1993 | European Pat. Off. . |
| 2644694 | 9/1990 | France . |
| 2160103 | 12/1985 | United Kingdom . |
| 2196834 | 5/1988 | United Kingdom . |
| 2197181 | 5/1988 | United Kingdom . |

*Primary Examiner*—David A. Simmons
*Assistant Examiner*—M. Curtis Mayes
*Attorney, Agent, or Firm*—Gerry S. Gressel; Larry L. Huston; E. Kelly Linman

[57] ABSTRACT

Described herein is a multiple layer absorbent core having a front ear section, a crotch section and a back ear section, wherein the machine direction length of the crotch section equals the combined machine direction length of the front ear section and the back ear section, the angle and radii forming the transition from the crotch width to the ear width being equal, the core being suitable for use in an absorbent article, and a method for manufacturing such multiple layer absorbent core. The method comprises providing a single web of absorbent core material from a roll, in which the web having parallel straight longitudinal side edges; continuously transporting the web of absorbent core material in the machine direction; continuously cutting the web of absorbent core material longitudinally into web sections having at least one full-pattern strip having a repeating hourglass-shape and first and second side trim pieces each of the side trim pieces having a straight edge defined by one of the parallel straight longitudinal side edges of the web and an opposite non-linear longitudinal edge having a pattern corresponding to one of the longitudinal edges of the full-pattern strip; continuously orienting the side trim pieces relative to the full-pattern strip such that the ear sections and said crotch section of the side trim pieces are superimposed in registration with said full-pattern strip to form a continuous multiple layer composite strip; and successively cutting the composite strip in the transverse direction at predetermined intervals to form discrete multiple layer absorbent cores.

17 Claims, 13 Drawing Sheets

U.S. PATENT DOCUMENTS

| | | | |
|---|---|---|---|
| 4,040,423 | 8/1977 | Jones, Sr. | 128/287 |
| 4,041,950 | 8/1977 | Jones, Sr. | 128/287 |
| 4,210,143 | 7/1980 | De Jonckheere | 128/287 |
| 4,259,958 | 4/1981 | Goodbar | 128/287 |
| 4,325,372 | 4/1982 | Teed | 128/287 |
| 4,381,782 | 3/1983 | Mazurak et al. | 604/368 |
| 4,425,127 | 1/1984 | Suzuki et al. | 604/366 |
| 4,439,260 | 3/1984 | Canterino et al. | 156/259 |
| 4,490,148 | 12/1984 | Beckestrom | 604/385 |
| 4,500,316 | 2/1985 | Damico | 604/389 |
| 4,518,451 | 5/1985 | Luceri et al. | 156/202 |
| 4,557,777 | 12/1985 | Sabee | 156/201 |
| 4,595,441 | 6/1986 | Holvoet et al. | 156/265 |
| 4,610,751 | 9/1986 | Eschler | 156/517 |
| 4,666,550 | 5/1987 | Spiers et al. | 156/361 |
| 4,670,011 | 6/1987 | Mesek | 604/378 |
| 4,670,960 | 6/1987 | Provost | 29/415 |
| 4,690,719 | 9/1987 | Lucas et al. | 156/201 |
| 4,704,115 | 11/1987 | Buell | 604/385 |
| 4,729,814 | 3/1988 | Jennus et al. | 156/512 |
| 4,731,071 | 3/1988 | Pigneul | 604/385 |
| 4,753,645 | 6/1988 | Johnson | 604/378 |
| 4,756,958 | 7/1988 | Bryant et al. | 428/320.2 |
| 4,760,764 | 8/1988 | De Jonckheere et al. | 83/23 |
| 4,781,710 | 11/1988 | Megison et al. | 604/378 |
| 4,787,896 | 11/1988 | Houghton et al. | 604/385.1 |
| 4,795,453 | 3/1989 | Wolfe | 604/385.1 |
| 4,822,435 | 4/1989 | Igaue et al. | 156/164 |
| 4,834,740 | 5/1989 | Suzuki et al. | 604/385.2 |
| 4,862,574 | 9/1989 | Seidy | 29/415 |
| 4,869,942 | 9/1989 | Jennus et al. | 428/77 |
| 4,900,317 | 2/1990 | Buell | 604/378 |
| 4,917,750 | 4/1990 | Klose | 156/254 |
| 4,950,355 | 8/1990 | Klose | 156/204 |
| 4,960,477 | 10/1990 | Mesek | 156/209 |
| 4,994,052 | 2/1991 | Kimura | 604/355 |
| 5,007,906 | 4/1991 | Osborn, III et al. | 604/385.1 |
| 5,021,051 | 6/1991 | Hiuke | 604/385 |
| 5,034,007 | 7/1991 | Igaue et al. | 604/365 |
| 5,064,489 | 11/1991 | Ujimoto et al. | 156/164 |
| 5,080,741 | 1/1992 | Nomura et al. | 156/201 |
| 5,102,487 | 4/1992 | Lamb | 156/260 |
| 5,110,386 | 5/1992 | Ochi et al. | 156/204 |
| 5,123,316 | 6/1992 | Niedermaier et al. | 83/29 |
| 5,134,007 | 7/1992 | Reising et al. | 428/78 |
| 5,151,091 | 9/1992 | Glaug et al. | 604/385 |
| 5,165,979 | 11/1992 | Watkins et al. | 428/113 |
| 5,295,988 | 3/1994 | Muckenfuhs et al. | 604/385 |
| 5,300,054 | 4/1994 | Feist et al. | 604/378 |

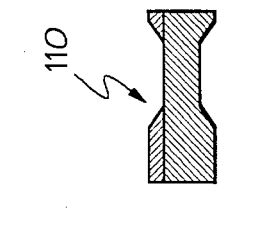
FIG. 5d
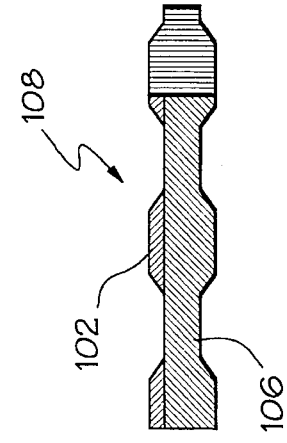
FIG. 5c
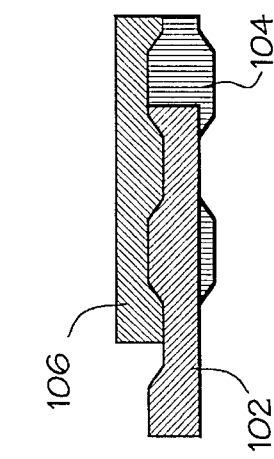
FIG. 5b
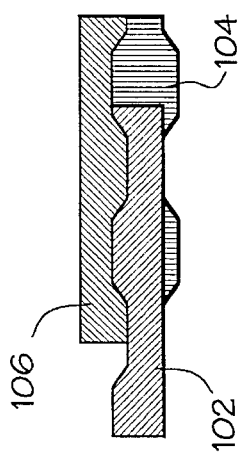
FIG. 5a
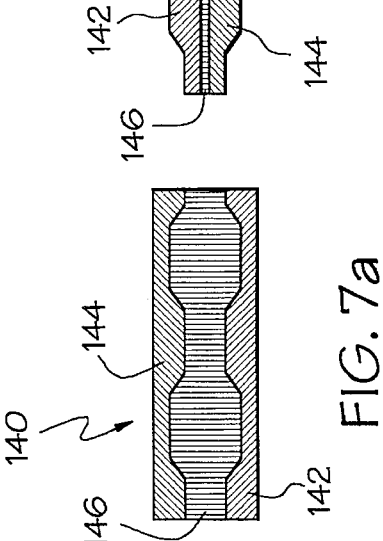
FIG. 7b
FIG. 7a
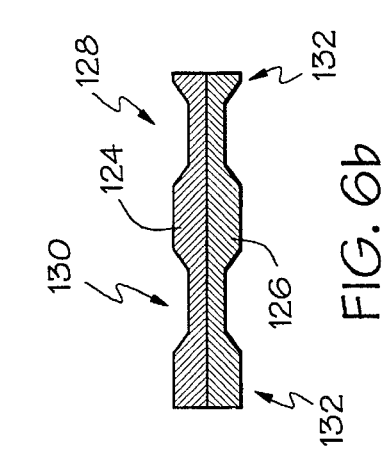
FIG. 6b
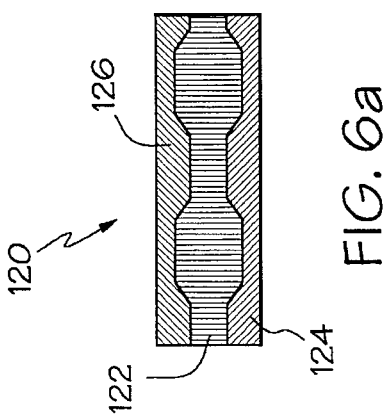
FIG. 6a

ZERO SCRAP ABSORBENT CORE FORMATION PROCESS

TECHNICAL FIELD

This present invention relates to shaped or contoured absorbent cores made from multiple pieces or layers, of absorbent material derived from web based materials that are useful in absorbent articles, such as diapers, adult incontinent briefs, sanitary napkins and the like. This application further relates to a process for making such shaped or contoured absorbent cores that essentially eliminates scrap generated in the production of shaped absorbent cores.

BACKGROUND OF THE INVENTION

Incontinence management articles, such as non-cloth disposable diapers, have traditionally utilized absorbent structures which comprise entangled masses of fibers, i.e. non woven fibrous webs. These webs imbibe aqueous fluids, including discharged body fluids, both by an absorption mechanism where fluid is taken up by the fiber material itself, and especially by a wicking mechanism where fluid is acquired by, distributed through and stored in the capillary interstices between the fibers. These webs often comprise loosely compacted, low density layers of absorbent fibers, such as carded cotton webs, air-laid cellulose fibers, comminuted wood pulp fibers, and the like.

Fibrous webs used in such absorbent articles also often include certain absorbent gelling materials usually referred to as "hydrogels," "super absorbent" or "hydrocolloid" materials to store large quantities of the discharged body fluids. See, for example, U.S. Pat. No. 3,699,103 (Harper et al), issued Jun. 13, 1972, and U.S. Pat. No. 3,770,731 (Harmon), issued Jun. 20, 1972, that disclose the use of particulate absorbent gelling materials in absorbent articles. Indeed, the development of thinner diapers has been the direct consequence of thinner absorbent cores that take advantage of the ability of these particulate absorbent gelling materials to absorb large quantities of discharged aqueous body fluids, especially when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and particulate absorbent gelling materials useful in fashioning then, compact, nonbulky diapers.

These particulate absorbent gelling materials are unsurpassed in the market place for their ability to retain large volumes of fluids, such as urine. A representative example of such particulate absorbent gelling materials are lightly crosslinked polyacrylates. Like many of the other absorbent gelling materials, these lightly crosslinked polyacrylates comprise a multiplicity of anionic (charged) carboxyl groups attached to the polymer backbone. It is these charged carboxyl groups that enable the polymer to absorb aqueous body fluids as the result of osmotic forces.

Besides osmotic forces, absorbency based on capillary forces is also important in many absorbent articles, including diapers. Capillary forces are notable in various everyday phenomena, as exemplified by a paper towel soaking up spilled liquids. Capillary absorbents can offer superior performance in terms of the rate of fluid acquisition and wicking, i.e. the ability to move aqueous fluid away from the point of initial contact. Indeed, the dual-layer absorbent core structures of Weisman et al and Lash et al noted above use the fibrous matrix as the primary capillary transport vehicle to move the initially acquired aqueous body fluid throughout the absorbent core so than it can be absorbed and retained by the particulars absorbent gelling material positioned in layers or zones of the core. The fibrous structures disclosed in Weisman et al and Lash et al are produced via air-laying technology. This technology involves air laying the fibers into shaped cavities on a screened drum to form the shape of the core and control the quantity of material used per core. Excess overfill of the shaped cavities is removed and returned to the incoming air stream by a scarfing roll. The Absorbent Gelling Materials (AGM) are added to the airstream along with the fiber materials. This process allows for many alternative shapes to be produced via changes in screen, laydown drum, configuration. Therefore the shape of the material is achieved via "Molding" the fibers into shaped cavities. This process provides shape without trim, which in turn results in minimal scrap.

An alternative absorbent material potentially capable of providing capillary fluid transport would be open-coiled polymeric foams. If made appropriately, open-celled polymeric foams could provide features of capillary fluid acquisition, transport and storage required for use in high performance absorbent cores for absorbent articles such as diapers. Absorbent articles containing such foams could possess desirable wet integrity, could provide suitable fit throughout the entire period the article is worn, and could avoid changes in shape during use. In addition, absorbent articles containing such foam structures could be easier to manufacture on a commercial scale. For example, absorbent diaper cores could simply be stamped out of continuous foam sheets and could be designed to have considerably greater integrity and uniformity than air-laid fibrous absorbent cores containing particulate absorbent gelling materials.

Besides absorbency and manufacturing ease, another potentially desirable property of such foams is the ability to make shaped or contoured absorbent cores having various shape configurations, fluid absorbency properties, etc. Fibrous absorbent cores containing particulate gelling materials have often been shaped or contoured, especially to provide hourglass-shaped configurations. See, for example, the dual-layer absorbent core structures of Weisman et al and Lash et al where the upper layer is in an hourglass-shaped configuration.

Shaped or contoured absorbent cores made from opencelled foam materials having particularly desirable fluid transport characteristics are disclosed in U.S. Pat. No. 5,147,345 (Young et al), issued Sep. 15, 1992. The Young et al absorbent core comprises a fluid acquisition/distribution component that can be fibrous or foam based, as well as fluid storage/redistribution component that comprises a hydrophilic, flexible, open-celled polymeric foam. FIG. 9 of Young et al discloses one such shaped or contoured core having an hourglass-shaped fluid acquisition/distribution layer 73 comprising a fibrous absorbent material overlying an hourglass-shaped fluid redistribution/storage layer comprising an open-cell absorbent foam. See also FIG. 2 which discloses a smaller rectangular fluid acquisition/distribution layer 51 comprising a fibrous absorbent material overlying a larger hourglass-shaped fluid redistribution/storage layer 52 comprising an open-celled polymeric foam.

Forming shaped or contoured absorbent cores or layers from foam materials, including those disclosed in Young et al, is not without problems. The hourglass-shaped foam layer shown in FIGS. 9 and 2 of Young et al is typically made from a single rectangular piece of foam. This rectangular piece of foam can be notched, cut or otherwise severed to form the hourglass-shaped piece. In carrying out these operations, a significant amount of unusable foam scrap can be created. Indeed, it has been found that, in forming hourglass-shaped foam pieces, as much as 15 to 25% of the total foam material used can end up as unusable scrap.

In addition, unitary hourglass-shaped foam pieces can create certain problems in terms of comfort of the absorbent article in which the absorbent foam core is used. In the case of higher modulus absorbent foams, hourglass-shaped unitary cores can be less soft and less flexible. This is especially true in the crotch area of an absorbent core made from a unitary hourglass-shaped absorbent foam layer. Accordingly, it would be desirable to be able to make shaped or contoured absorbent cores from polymeric foams that: (1) reduce generation of foam scrap; and (2) provide greater softness and flexibility, especially in the crotch area.

Previous product designs for shaped absorbent core structures generated from rectilinear roll stock, web, materials have generally produced significant amounts of scrap which must be discarded or recycled during the manufacturing process. Designs which utilize multiple rolls of various width material to generate shape are sometimes difficult to execute, specifically when they utilize very narrow webs of material. Large rolls of narrow webs are very difficult to manufacture and equally difficult to process into absorbent articles.

Attempts have been made previously to reduce the amount of scrap material produced during the manufacture of patterned articles derived from a continuous web. For example, each of U.S. Pat. No. 4,760,764 to Jonckheere et al. and EP 0539 032 A1 to Johnson & Johnson describe a manufacturing method with a reduced amount of waste material in which a continuous web of material is continuously cut in a cyclic pattern to provide two strips, each having a patterned longitudinal edge and a straight edge. The strips are cross directionally displaced, phased such that the tabs are aligned and then joined together in an overlapping fashion to form a two layered central region producing the edge contour of the final disposable absorbent product. Such products are limited to a single design structure having only two layers in the central region with only a single layer in the ear or tabular areas. Although this pattern could be repeated again on top of itself, the number of layers in the central region will be twice that of the layers that are present in the outer shaped regions. Such an arrangement although potentially effective from a fluid absorption standpoint, is less desirable from a stiffness, flexibility, overall thickness and crotch bulk minimization standpoint.

U.S. Pat. No. 3,072,123 (Davis), Jan. 8, 1963, shows a plurality of adjacent wave-like cutting lines forming nested shapes which are then further processed to form an absorbent article. Since this application is essentially intended to produce a unitary structure from the nested shapes, the outermost, partial, shapes provide no usefulness and therefore result in scrap material. This approach is unlike that of the present which utilizes the partial shaped segments as well as the full shapes, therefore resulting in essentially "Zero scrap." U.S. Pat. No. 3,878,286 (Jones), Apr. 15, 1975 is intended to produce a nested absorbent structure, however, as in U.S. Pat. No. 3,072,123, the outermost areas of the web which contain only partial structures or shapes, lacks usefulness and therefore results in scrap material. U.S. Pat. No. 4,862,574 (Seidy), Sep. 5, 1989, illustrates a method of producing a panty protector. Although this application does show a repeating cutting pattern or wave type pattern, the pattern is cross direction and not continuous in the machine or web, direction. Therefore, the approach of U.S. Pat. No. 4,862,574, produces discrete components versus the intent of the present invention which is to produce a continuous pattern resulting in multiple webs of product shapes in a continuous web. The cutting pattern incorporated in U.S. Pat. No. 4,862,574 results in partial structures which, as in the previously noted patents, provide no usefulness with respect to their respective inventions. U.S. Pat No. 3,527, 221 (Croon et al), Sep. 8, 1970, shows a wave-like cutting pattern utilized to shape the outer covering, chassis, of a diaper. Although this approach results in minimal scrap, it is not applied to the absorbent structure itself and it also involves no layering of the separated structures as in the present invention.

U.S. Pat Nos. 5,102,487; 5,034,007; 4,595,441 and 5,330,598 describe continuous strips of materials in conjunction with repeating patterns none of these inventions are intended to provide absorbent core structures. Also, none of the aforementioned patents involve more than two strips of material as does the present invention.

Furthermore, none of prior art references teach the manufacture of an absorbent core structure having a plurality of layers of absorbent material in the crotch area and the "ear" or tabular region, wherein the absorbent core structure is formed from a single web, while eliminating scrap formation.

It is, therefore, a major object of the present invention to provide a manufacturing method for producing an absorbent core material from a single web of material so that there is "zero scrap".

It is another object of the present invention to provide a manufacturing method for producing an absorbent structure having at least two layers of an absorbent core material in both the crotch area and the "ear" portions of the absorbent structure in which the core structure is formed from a single web of absorbent material.

It is another object of the present invention to provide a manufacturing method for producing a variety of absorbent core structures from a single web of absorbent material having different configurations depending upon the desired use of such absorbent cores.

It is still another object of the present invention to provide an absorbent core structure having improved absorbent efficiency and greater softness and flexibility for use in the production of diapers, incontinent products, etc.

SUMMARY OF THE INVENTION

In accordance with the present invention, a single roll of an absorbent material having a predetermined width is fed into a die cutter, such as a rotary knife, where one or more specific patterns are cut (along with a grouping of intermittent slits) and the single web is separated into three or more individual webs, depending upon the product design. By designing the pattern cut-out such that certain constraints are met as defined later, the various strips or pieces can be cut and aligned so that they nest exactly and conform precisely to the desired final core product.

The present invention not only provides a method for the manufacture of an efficient absorbent core material from a single roll of material but it also provides a product where the shape produces better fit and the multi-layering produces greater product softness and flexibility during wear. By utilizing multi-layering, the web thickness can be minimized and, thus, the amount of material used in manufacturing the core in maximized, lowering shipping and storage costs. Furthermore, the present method provides for the manufacture of such absorbent core materials without substantial accumulation of scrap material, thereby eliminating the need for an additional step for discarding or recycling excess material.

In order to achieve zero scrap, the following constraints should be maintained in forming the configuration of the core material as illustrated in FIG. 21:

(1) The most important constraint is the longitudinal distances of the crotch and ear sections. With reference to FIG. 21, the distance b=a+c where a is the distance from the front edge of the front core ear to the midway point through the transition between the front core ear and the core crotch, the distance b is from the midway point of the transition between the front core and the core crotch to the midway point of the transition between the core crotch and the rear core ear, and the distance c is from the midway point of the transition between the core crotch and the rear core ear to the end of the rear core ear;

(2) The front ear width equals the rear ear width; and (3) The transitions between the ears and the crotch must be symmetrical.

In a first embodiment of the invention, a single width web of absorbent material such as a foamed absorbent material is fed from a roll into a die cutter to provide one main web cutout having the desired pattern of the final product and two trim pieces formed along the lateral edges of the web wherein the trim pieces are transported to a position on top of the full pattern strip. In accordance with one aspect of this embodiment, the two trim pieces are placed on top of the full pattern strip in a full overlay format where the core has three layers of absorbent material in the entire crotch portion and two layers of absorbent material in the core ears. In one manifestation, the two trim pieces are placed in a partial overlay where the core has three layers in the central longitudinal region of the crotch area and two layers in the lateral longitudinal regions of the crotch area and two layers in the core ears.

In a second aspect, the two trim pieces are in the same plane. As a first manifestation, the two trim pieces of absorbent material are placed in a "butting" format where the core has two layers of absorbent material in the entire crotch area and two layers in the core ears. As a second manifestation, the two trim pieces are placed in a "gap" format where the core has a single layer of absorbent material in the central longitudinal area of the crotch and two layers of material in the lateral longitudinal areas of the crotch and the core ears. For the purpose of this invention, "butting" means that the trim pieces are intended to touch along the straight edges of the trim pieces. The term "gap" is intended to mean that the straight edges of the trim pieces do not touch and the trim pieces do not overlap. Alternately, the two trim pieces may be separated from the web and oriented with their straight longitudinal edges juxtaposed each other to form the desired pattern first and then the full pattern strip may be subsequently superimposed upon the trim pieces.

In a second embodiment of the invention, a single width sheet of absorbent material is fed from a roll into a die cutter to provide two main webs juxtaposed to each other along a common central edge and offset from one another so that the tabs of one web corresponds exactly to the notches of the other web, each web having the desired pattern of the final product; and two trim pieces formed along the lateral edges of the web wherein the trim pieces are transported to a position where they may be sandwiched between the two web cutouts in a full or partial overlapping format to provide a core having four layers of absorbent material in the crotch portion and three layers of absorbent material in the core ears, or in a "butt" or "gap" format to provide a core having three or two layers, respectively, of absorbent material in the crotch portion and three layers of absorbent material in the core ears. Alternatively, the trim pieces may be transported to a position on top of or under the two main webs in a partial or full overlap configuration or in a "butt" or "gap" format.

In a third embodiment of the invention, a single width web of absorbent material is fed from a roll into a die cutter to provide one main web cutout having the desired pattern of the final product and two trim pieces formed along the lateral edges of the web wherein the trim pieces are twisted or rotated 180° prior to being superimposed on the full pattern strip. In this embodiment, the upper surface of the side trim piece faces the upper surface of the full pattern strip. As in the first and second embodiments, the two side trim pieces may be positioned on top of the full pattern strip in a full overlay format or in a partial overlay format to provide a first aspect of the third embodiment where the core has three layers of absorbent material in the crotch portion and two layers of absorbent material in the core ears, or the two trim strips may be in the same plane such as in a "butting" or "gap" format to provide another aspect of this embodiment.

In another embodiment of the invention, a single width sheet of absorbent material is fed from a roll into a die cutter to provide two main webs juxtaposed to each other along a common central edge and offset from one another so that the tabs of one web corresponds exactly to the notches of the other web, each web having the desired pattern of the final product; and two trim pieces formed along the lateral edges of the web wherein the trim pieces are transported to a position where they sandwich the two web cutouts in a full or partial overlapping format to provide a core having four layers of absorbent material in the crotch portion and three layers of absorbent material in the core ears, or in a "butt" format or a "gap" format to provide a core having two or three layers of absorbent material in the crotch portion and three layers of absorbent material in the core ears. Alternatively, the trim pieces may be transported to a position on top of the two main webs in a partial or full overlap configuration or in a "but" or "gap" format.

BRIEF DESCRIPTION OF THE DRAWINGS

While the specification concludes with claims particularly pointing out and distinctly claiming the subject matter of the present invention, it is believed that the invention will be better understood from the following description and the drawings, in which like reference numerals identify identical elements.

FIGS. 5a–5d are top plan views of a single width web of absorbent material showing a pattern cutout in accordance with one aspect of the first embodiment of the invention in which the trim pieces overlap;

FIGS. 6a–6b are top plan views of a single width web of absorbent material showing a pattern cutout in accordance with another aspect of the first or second embodiment of the invention in which the trim pieces abut;

FIGS. 7a–7b are top plan views of a single width web of absorbent material showing a pattern cutout in accordance with another aspect of the first or second embodiment of the invention in which the trim pieces form a gap;

DETAILED DESCRIPTION OF THE INVENTION

The structures of the present invention will be described in relationship to their use as absorbent cores in disposable diapers, adult incontinence products, catamenials and the like; however, it should be understood that the potential application of the structures of the present invention should not be limited to only absorbent core structures or such aforementioned disposable articles. Herein after, the term "Disposable absorbent article" refers to any article which absorbs and contains body exudates, such as: urine, fecal material, menses, blood and the like. More specifically, this term refers to any article which is placed against or in proximity to the body of the wearer to absorb and contain the various exudates discharged from the body, and additionally is intended to be discarded after a single use (i.e., the articles are not intended to be laundered or otherwise restored or reused). In a preferred aspect of the invention, the disposal absorbent core structure is employed in a diaper product. As used herein the term "diaper" refers to an undergarment generally worn by infants and incontinent persons and is worn about the lower torso of the wearer. In general, disposable diapers comprise a liquid pervious topsheet, a liquid impervious backsheet joined with the topsheet and an absorbent core structure positioned between the top sheet and the back sheet.

The present invention relates to the absorbent core structure and particularly, to a method for manufacturing an absorbent core structure having "zero scrap", thus eliminating the steps for disposing or recycling surplus material.

Traditionally, a web of absorbent material is controlled by putting energy into the web. This is accomplished by pulling the web at various places via nips, S wraps, etc. and the web, in turn, drives other rolls which include idlers, tracking devices, etc. Because of the hysteresis of certain absorbent materials which may be highly visco elastic, it is important that the web material be placed under minimum strain and, preferably, the strain should not exceed about 1%.

Figure 3:
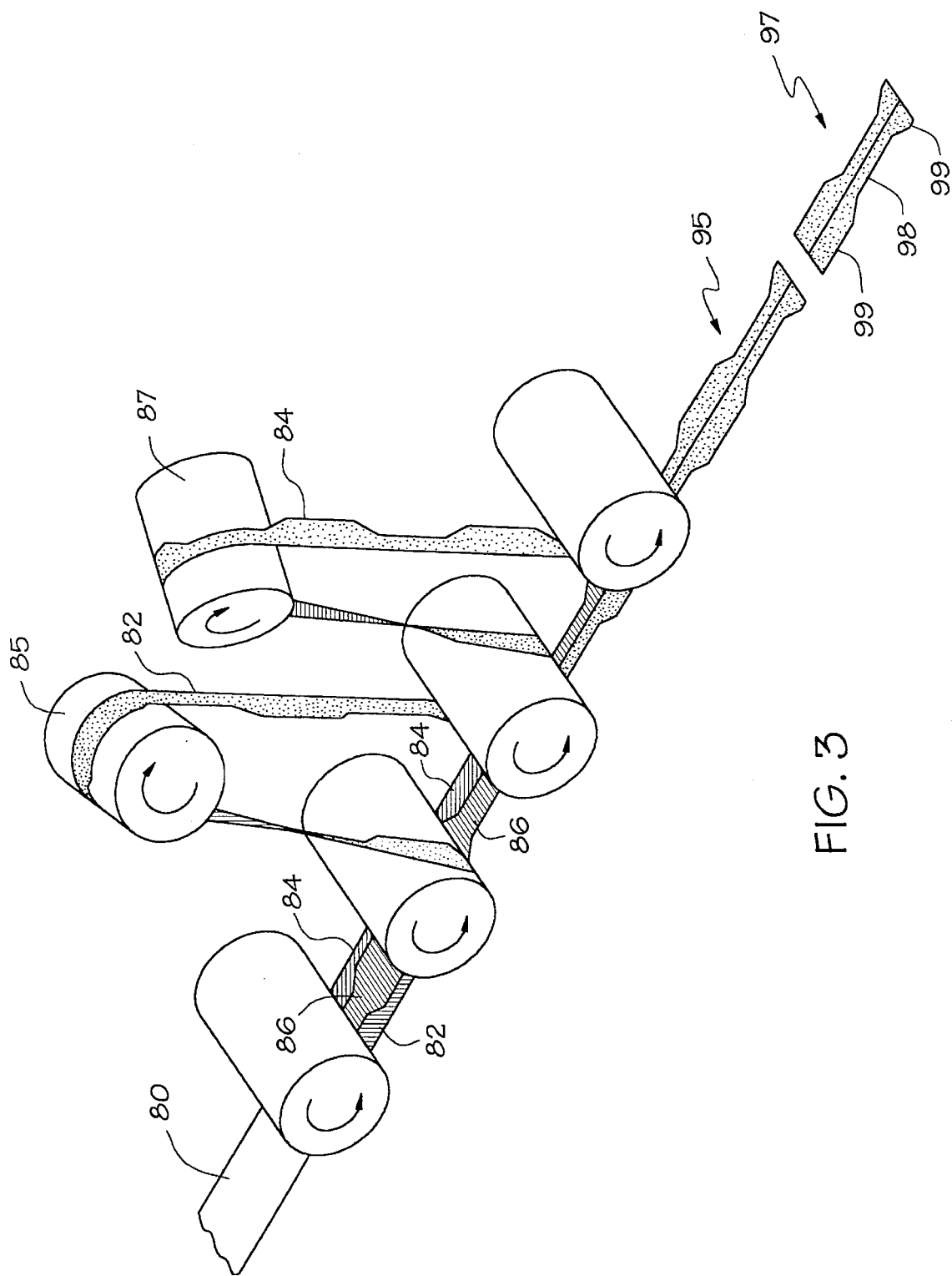
FIG. 3 is a perspective view illustrating another method for manufacturing the absorbent core of the present invention.

In accordance with the present invention, each of the rolls in the core-forming apparatus is independently driven so that the driving energy is not dependent upon the web material. If all rolls are driven at the same speed, no strain is imparted to the web and, in order to maintain sufficient web tension, the speed of each roll should be no more than 1% faster than the preceding roll. Even when all rolls are driven at the same speed, there are still places where the web undergoes some strain. Strain is imparted when the web goes over a roll, and when the web is twisted during the phase shift. The strain may be kept under 1% when going over a roll by proper selection of the roll diameter. Knowing the web thickness, the strain can be set to 1% and the minimum roll diameter can be calculated by the formula:

$$d = \frac{2t(1-\epsilon)}{\epsilon}$$

where t is the web thickness and e is the strain. The diameter should be greater or equal to "d". The strain in the web is also maintained under 1% during the twist by selecting a minimum height of the twist roll by calculating the different path lengths of the center of the web, and the edges of the web as the web goes through a helix, setting the strain at the edge to 1% and back for the minimum distance h. The helix that the web goes through (as illustrated in FIG. 3) is also determined by the angle α of the twist roll. The angle α is determined by:

$$\alpha = \arcsin\left(\frac{c}{d}\right)$$

This equation only works if the web path is perpendicular to the rolls as it is twisted. The height of the twist roll, h is determined by:

$$h = \frac{[n(\text{core} - \text{length}) + b - \pi d]}{2}$$

Where b is the distance between rolls. Note that n is an independent variable and can be any integer. It represents the number of cores the trim piece is phase shifted back. It (n) must be selected so that h is greater than the minimum h determined earlier.

The trim rolls are not fixed in place. They can rotate to keep the trim pieces properly tracked as they're laid on top of the main web. The placement of this roll, and the vertical axis it rotates about are very important for proper web control and tracking. The web wants to be perpendicular to the roll, and will track towards that position.

During the twist, the center line of each trim piece must remain tangent and perpendicular to each roll and to the new (or previous) web path. The rolls are sized and spaced so that this constraint is maintained. This determines the roll separation distance b.

The axis about which the twist roll rotates is the same as the center line of the trim piece. This way, the geometrical relationship between the trim piece, and twist roll is always maintained (at the input side of the roll). This is somewhat similar to a Fife® unit which is a web handling industry tracking device. The present system is different in that it uses driven rolls (Fife's® use idlers); uses three rolls (Fife's® use four); in the roll diameter (Fife's® use approximately 3" diameter rolls); and in the vertical axis of rotation of the tracking unit.

Figure 1:
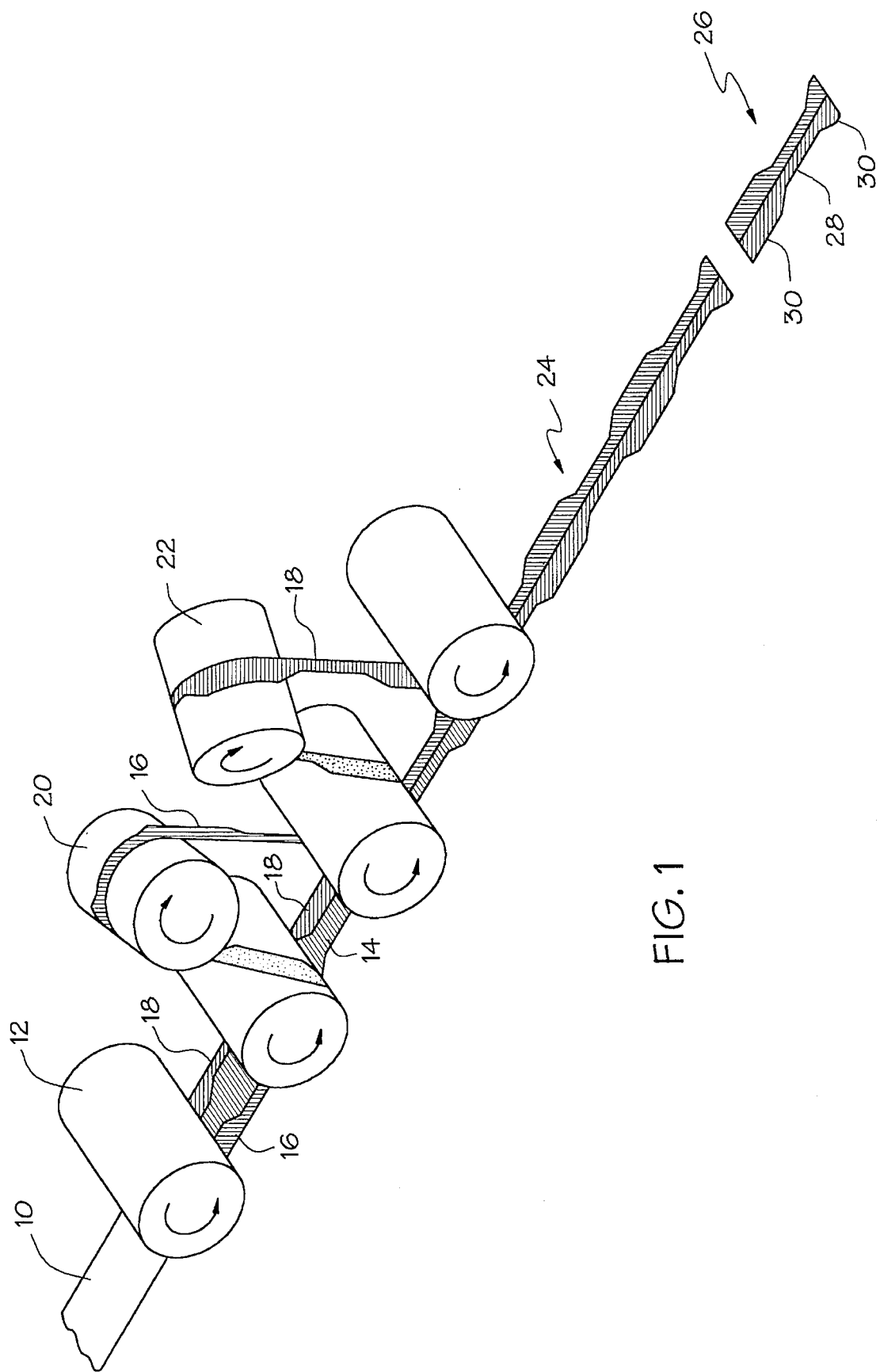
FIG. 1 is a perspective view illustrating a method for manufacturing the absorbent core of the present invention.

As illustrated in FIG. 1, a uniform web 10 of absorbent material, fed from a single roll (not shown), is cut into a desired pattern by a rotary die 12 or other means to provide a full pattern cutout 14, a first trim piece 16 and a second trim strip 18 in accordance with one embodiment of the invention. After the web is cut into the three patterned webs (1 main patterned cutout and 2 trim pieces), the main pattern cutout 14 continues in the same plane as the original web 10, while the first outer trim piece 16 is twisted and guided by a first elevated driven roll 20 angled relative to the machine centerline such that first trim piece 16 is superimposed in registration on the full pattern cutout 14. By virtue of the longer lengths traveled by first trim piece 16 relative to the full pattern cutout 14, the first trim piece 16 shifts in the machine direction and aligns with the full pattern cutout 14. Just prior to combining the full pattern cutout 14 and the first trim piece 16, an adhesive bonding material may be applied continuously or intermittently to the upper surface of the full pattern cutout 14 or to the lower surface of the first trim piece 16 or to both surfaces to temporarily join the layers together during processing. Other bonding methods, such as thermal bonding, which are known in the art may be used in place of an adhesive material.

The second trim piece 18 undergoes a similar transformation (in mirror image) as the first trim piece 16 at second elevated roll 22. The combined web 24 continues to be transported in the machine direction to a cutting operation and a speed up conveyor to separate the web into a discrete core structure 26 having three layers of absorbent material in the crotch portion 28 of the discrete core structure 26 and two layers of absorbent material in the "ears" 30 the core structure 26.

Figure 2:
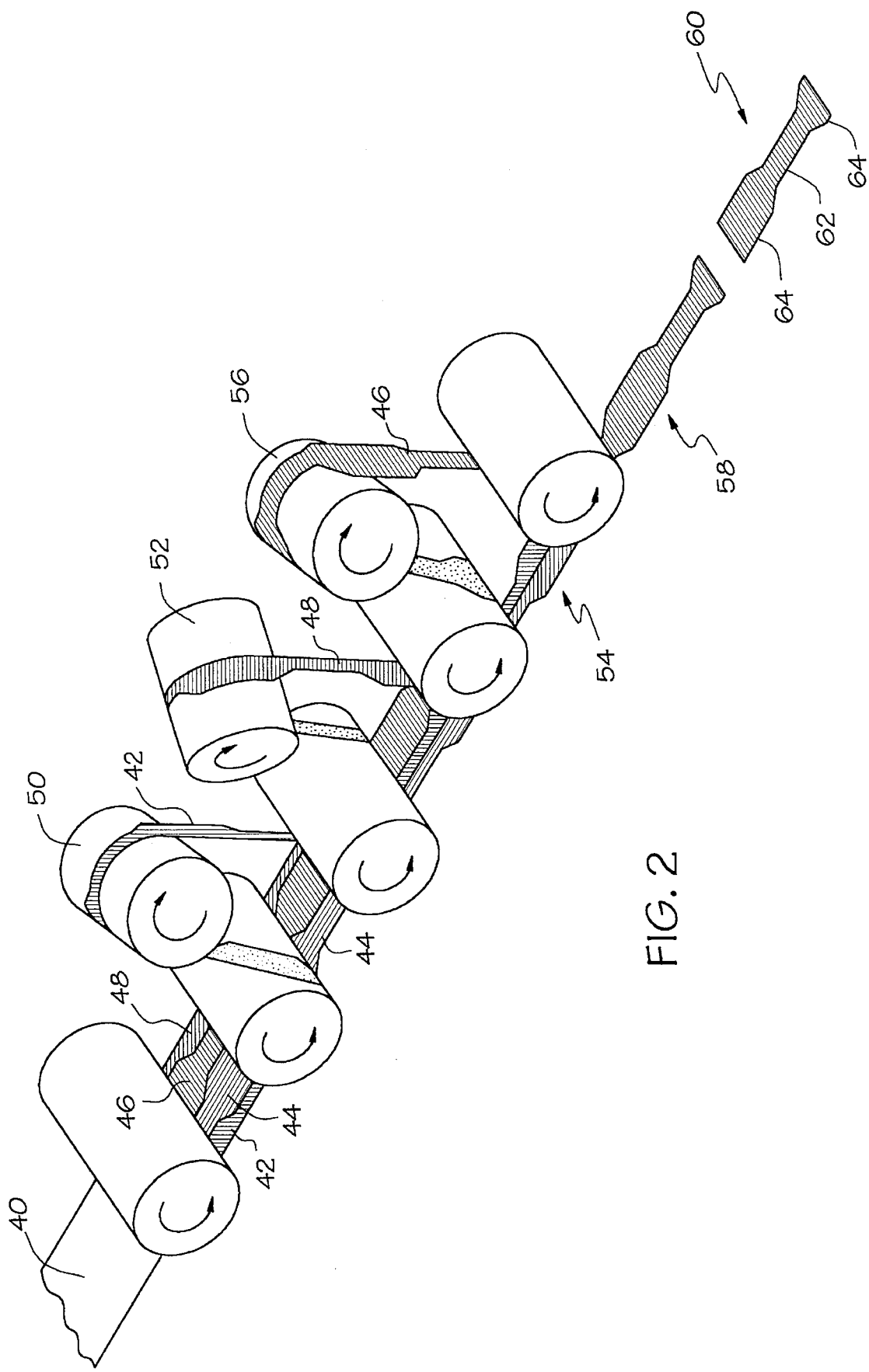
FIG. 2 is a perspective view illustrating a variant of the method shown in FIG. 1.

As illustrated in FIG. 2, a uniform web 40 of absorbent material having a slight broader width than the web shown in FIG. 1 is cut into a first trim strip 42, a first full pattern strip 44, a second full pattern strip 46 and a second trim strip 48. After the web 40 is cut into the four patterned strips (2 trim strips and 2 full pattern strips), the full pattern strips and the second trim strip continues in the same plane as the original web 40, while the first trim strip 42 is twisted and guided by a first elevated roll 50 angled relative to the machine centerline such that first trim strip 42 is superimposed on the first full pattern strip 44 or the second full pattern s trip 46. By virtue of the longer lengths traveled by the first trim strip 42 relative to the first full pattern strip 44, the first trim strip shifts in the machine direction and aligns with the first full pattern strip 44. Just prior to combining the first full pattern strip 44 and the first trim strip 42, an adhesive bonding material (not shown) may be applied continuously or intermittently to the upper surface of the full pattern strip 44 or the lower surface of the first trim strip 42 or to both surfaces to temporarily join the layers together during processing.

As the first trim strip 42 is superimposed on the first full pattern strip 44, the second trim strip 48 undergoes a similar transformation (in mirror image) as the first trim strip 42 at the second elevated roll 52 as the first combined web 54 continues to be transported in the machine direction. As the second trim strip 48 is superimposed on the first full pattern strip 44, the second full pattern strip 46 is picked up by the third elevated roll 56 and subsequently superimposed on the first full pattern strip 44 such that the first and second trim strips 42 and 48, respectively, are positioned between the first and second full pattern strips 44 and 46, respectively to form second combined web 64. The composite structure 58 containing the two full pattern strips and the two trim strips continues to the cutting operation (not shown) and a speed up conveyor to separate the composite web 58 into discrete core structure 60 having two, three or four layers of absorbent material in the crotch portion 62 of the discrete core structure 60 and three layers of absorbent material in the "ears" 64 of the discrete core structure 60.

Figure 4:
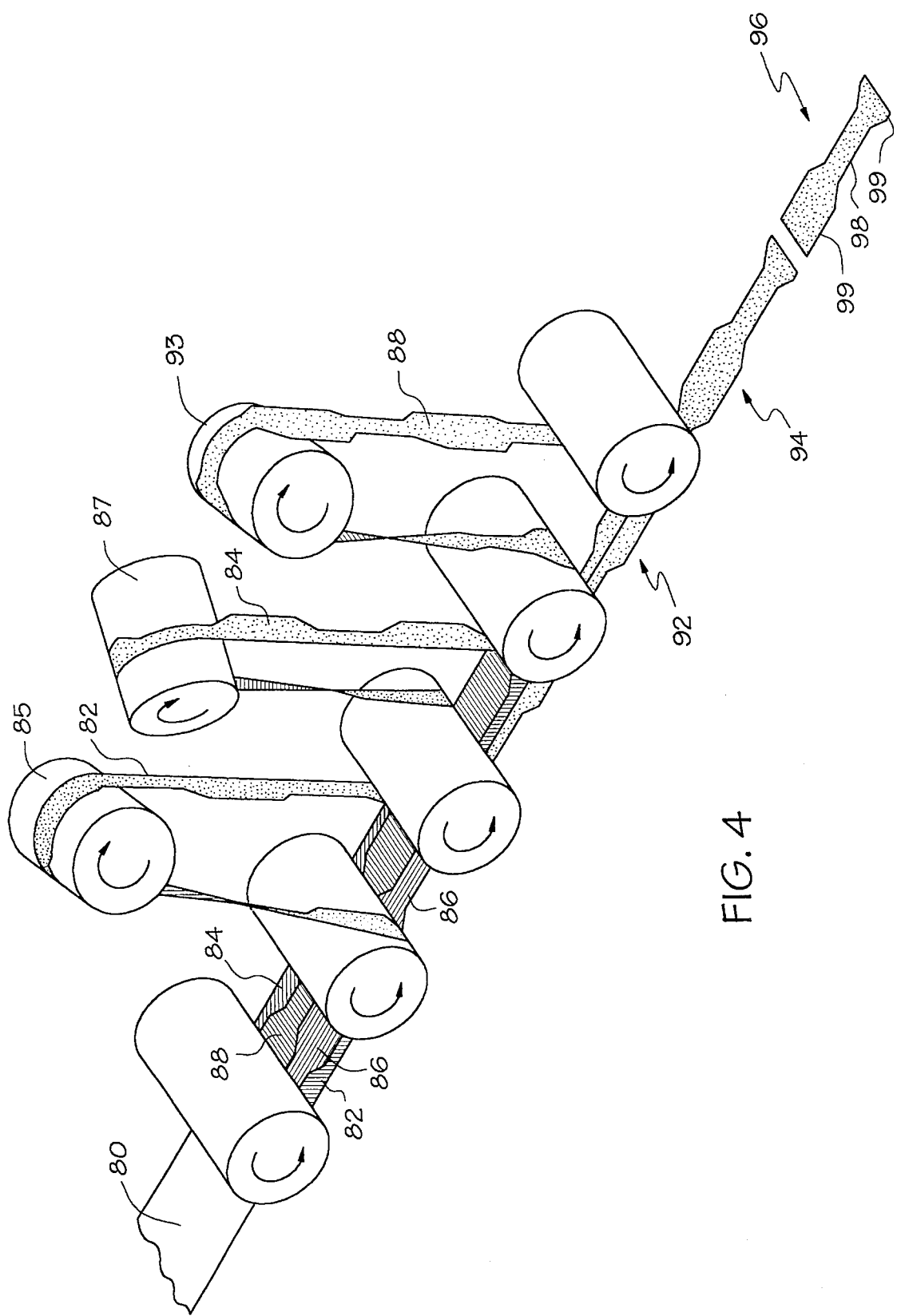
FIG. 4 is a perspective view illustrating a variant of the method shown in FIG. 3.
Figure 8A:
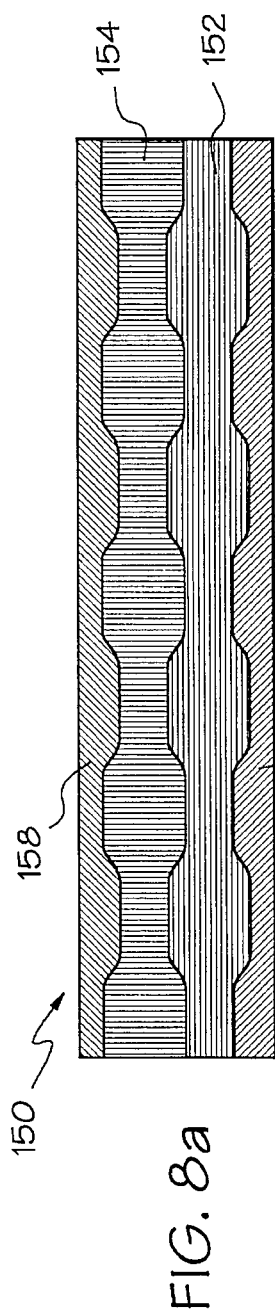
FIGS. 8a–8d are top plan views of a single width web of absorbent material showing a pattern cutout in accordance with another aspect of the second embodiment of the invention.
Figure 8B:
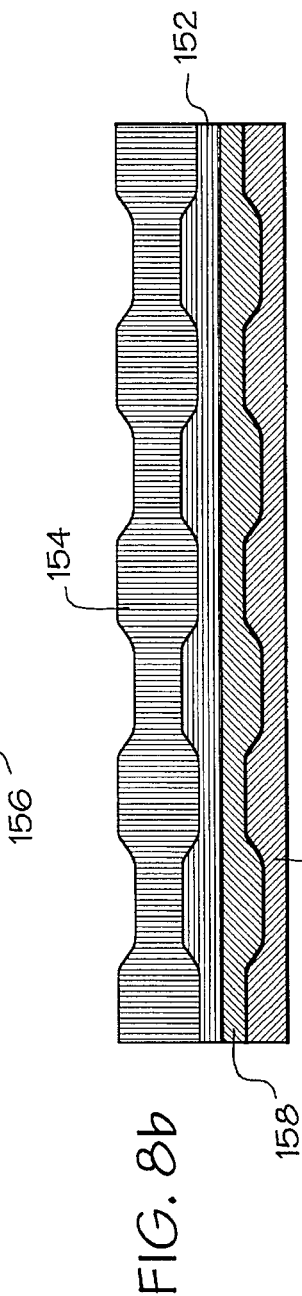
Figure 8C:
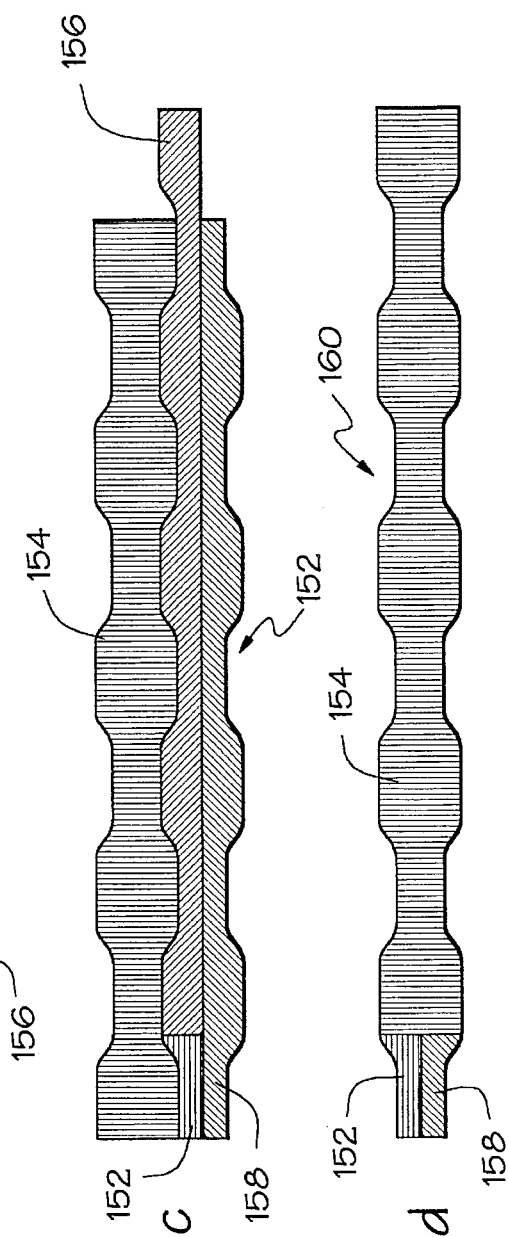
Figure 8D:
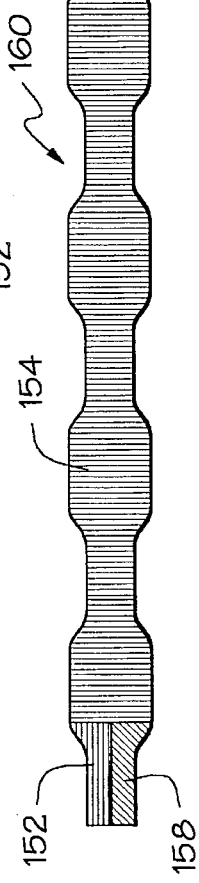

FIGS. 3 and 4 are similar to FIGS. 1 and 2 except that the web 80 is transported in the machine direction and as the first trim strip 82 and second trim strip 84 are picked up by elevated rollers 85 and 87, respectively, the first trim strip 82 and the second trim strip 84 are twisted 180° so that when they are superimposed on the full pattern strip 86, the top surface of the trim strips face the top surface of the full pattern strip 86. The first side trim piece may be twisted 180° prior to or subsequent to being transported over the second horizontal roll and the second sidetrim piece may be twisted 180° prior to or subsequent to being transported over the fourth horizontal roll. As shown in FIG. 4, a second full pattern strip 88 is pickup by the third elevated roll 93 and superimposed on the combined web 92 to form a composite web 94 containing the first and second trim strips 82 and 84, respectively, positioned between the first full pattern strip 86 and the second full pattern strip 88. The composite web 94 (FIG. 4) and 95 (FIG. 3) are cut into discrete core structure 96 (FIG. 4) and 97 (FIG. 3) each having a crotch portion 98 and ear portion 99.

FIGS. 5a–5d illustrate a uniform web 100 having two longitudinal cuts therein to provide a first trim strip 102, a full pattern strip 104 and a second trim strip 106. FIG. 5b shows the first trim strip 102 superimposed on the full pattern strip and FIG. 5c shows the second trim strip 106 superimposed on the full pattern strip in which first trim strip 102 and the second trim strip 106 overlap to form a combined web structure 108. FIG. 5d shows the cut discrete core structure 110.

As illustrated in FIGS. 6a–6b, a uniform web 120 having a slightly narrower width than the web shown in FIGS. 5a–5d is cut into a full pattern strip 122, a first trim piece 124 and a second trim piece 126 and assembled in a manner similar to that used to provide the core structure of FIGS. 5a–5d except that first trim piece 124 and the second trim piece 126 are abutted against each other along a straight edge to provide a combined web structure 128. The combined web has two layers of absorbent material in the crotch portion 130 of the core structure and two layers of absorbent material in the "ears" portion 132 of the core structure. While this embodiment is illustrated as having the two trim pieces butted together, it is also within the concept of the present invention to employ an even more narrow web material 140 to provide even thinner first and second trim pieces 142, 144, respectively, so that when the two trim pieces are "rested" on top of the full pattern cutout 146, they are preferably spaced apart rather than being in an abutting configuration. This concept is illustrated in FIGS. 7a–7b.

FIGS. 8a–8d illustrate second or fourth embodiments of the present invention in which a uniform web 150 of absorbent material is to provide a first full-pattern cutout 152, a second full-pattern strip 154 simultaneously formed in an offset format, a first trim piece 156 and a second trim piece 158. In this embodiment, the first trim piece 156 and the second trim piece 158 are assembled to provide a full-pattern composite 152 having the first trim piece 156 and the second trim piece 158 "resting" on top of the full pattern strip 152 in which the first trim piece 156 and the second trim piece 158 are abutted against each other along a straight edge. With the first full pattern strip 152 and the two trim pieces 156, 158 in place, the second main pattern strip 154 aligns with the first full pattern strip 152 to further provide the desired pattern where the first trim piece 156 and the second trim piece 158 are abutting each other along their straight edges, and are sandwiched between the first full pattern strip 152 and the second full center strip 154 to provide a combined web structure 160 in which all of the components are aligned in the desired design format. The combined web 160 is then cut transversely and separated into discrete core structure having three layers of absorbent material in the crotch portion of the core structure and three layers of absorbent material in the "ears" of the core structure.

Figure 9:
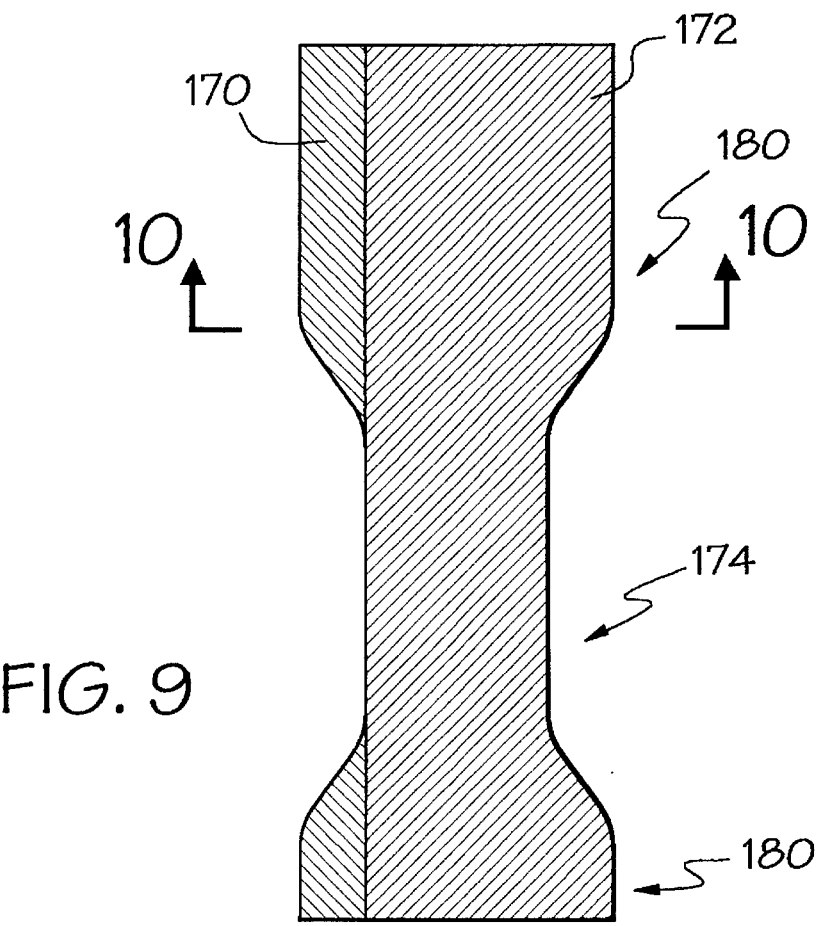
FIG. 9 is a top plan view illustrating an absorbent core structure in accordance with one aspect of the first embodiment of the invention showing the overlapping trim pieces in a full overlay format.
Figure 10:
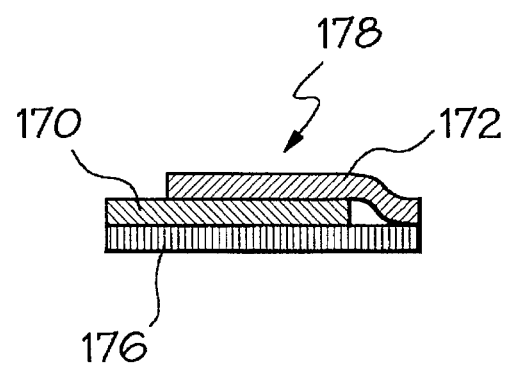
FIG. 10 is a cross-sectional view of the absorbent core structure of FIG. 9 taken along section line 10—10.

The embodiments of the present invention and the multiple configuration of each of the embodiments are better understood by referring to FIGS. 9-18 of the drawings in which FIGS. 9 and 10 illustrate an aspect of the first embodiment of the invention where the first trim strip 170 and the second trim strip 172 each extend the full width of the crotch portion 174 on top of the full pattern strip 176, the second trim piece 172 overlaying the first trim piece 170. As seen in FIG. 10, the resulting core structure 178 has three layers of absorbent material in the crotch portion 174 of structure 178 and two layers of absorbent material in the "ears" 180.

Figure 11:
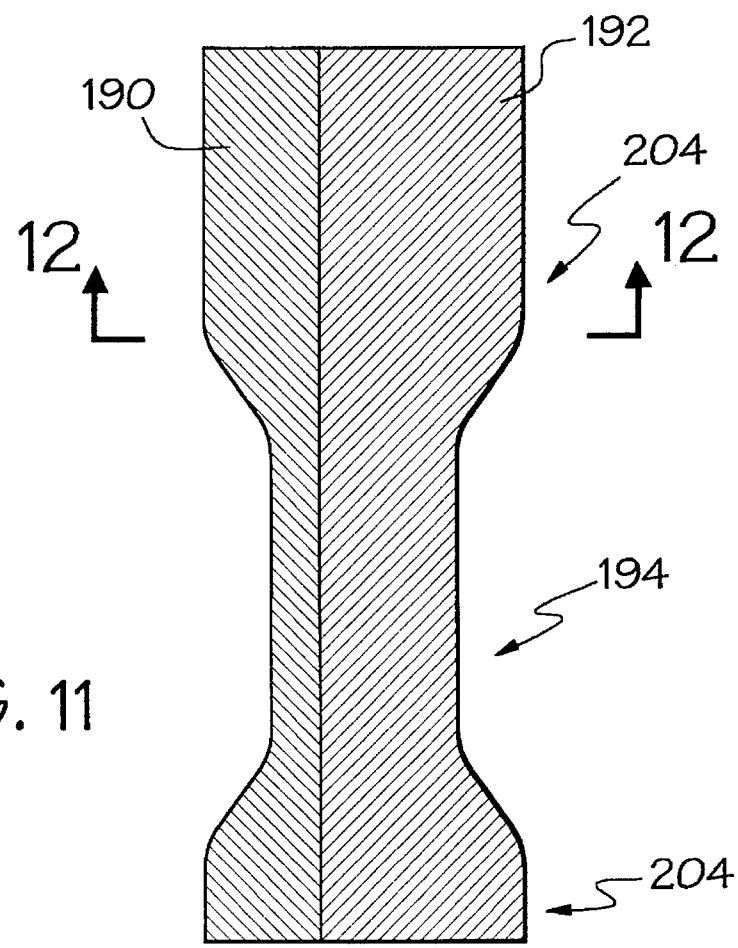
FIG. 11 is a top plan view of illustrating an absorbent core structure in accordance with another aspect of the first or second embodiment of the invention showing the overlapping trim pieces in a partial overlay format.
Figure 12:
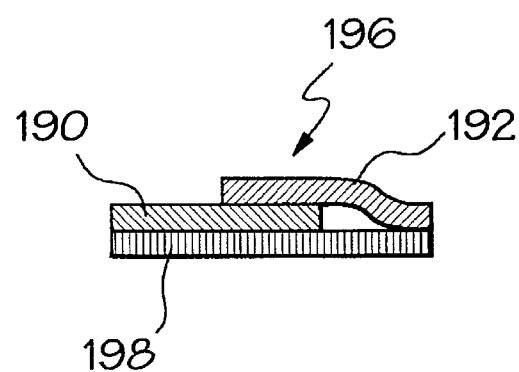
FIG. 12 is a cross-sectional view of the absorbent structure of FIG. 11 taken along section line 12—12.

In another configuration as illustrated in FIGS. 11 and 12 of the invention, the first trim strip 190 and the second trim strip 192 each extend only a partial width of the full pattern strip 198 in the crotch portion 194. As seen in FIG. 12, the resulting core structure 196 has three layers of absorbent material in the central part of the crotch portion while the outer edges of the crotch portion and the "ears" 204 have two layers of absorbent material.

Figure 13:
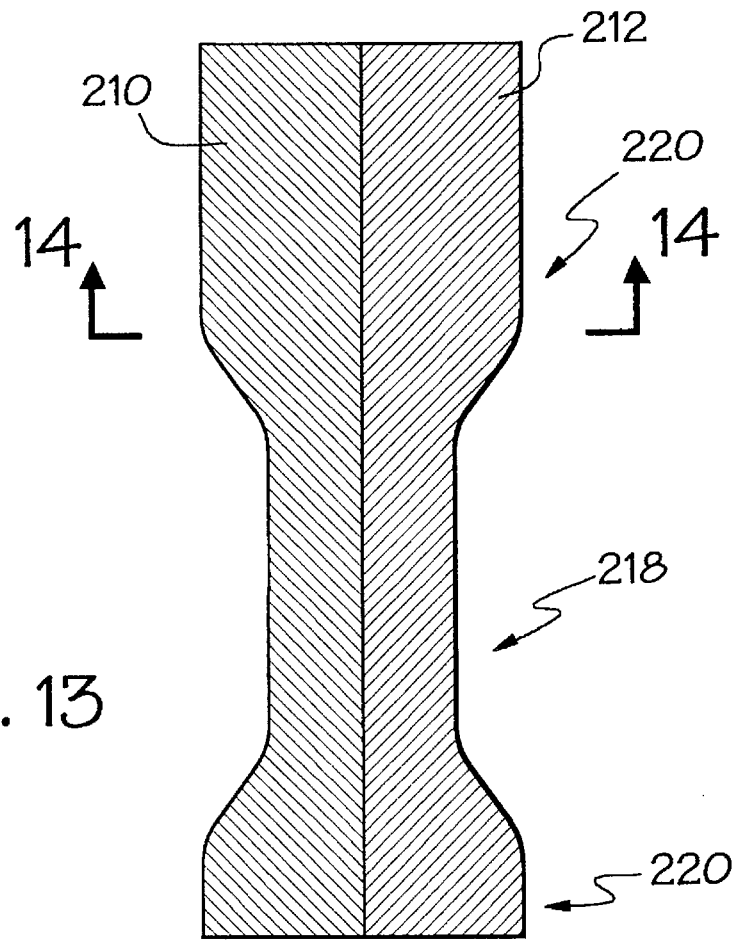
FIG. 13 is a top plan view illustrating an absorbent in accordance with another aspect of the first or second embodiment of the invention showing the two trim pieces in an abutting format.
Figure 14:
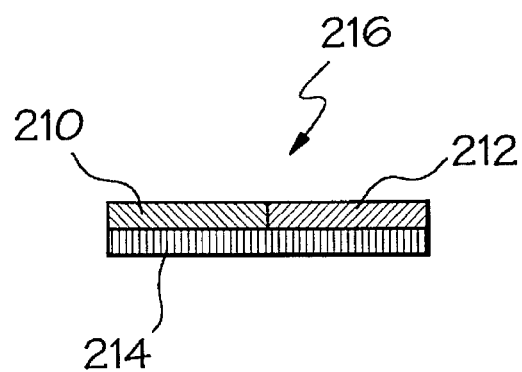
FIG. 14 is a cross-sectional view of the absorbent core structure of FIG. 13 taken along section line 14—14.
Figure 15:
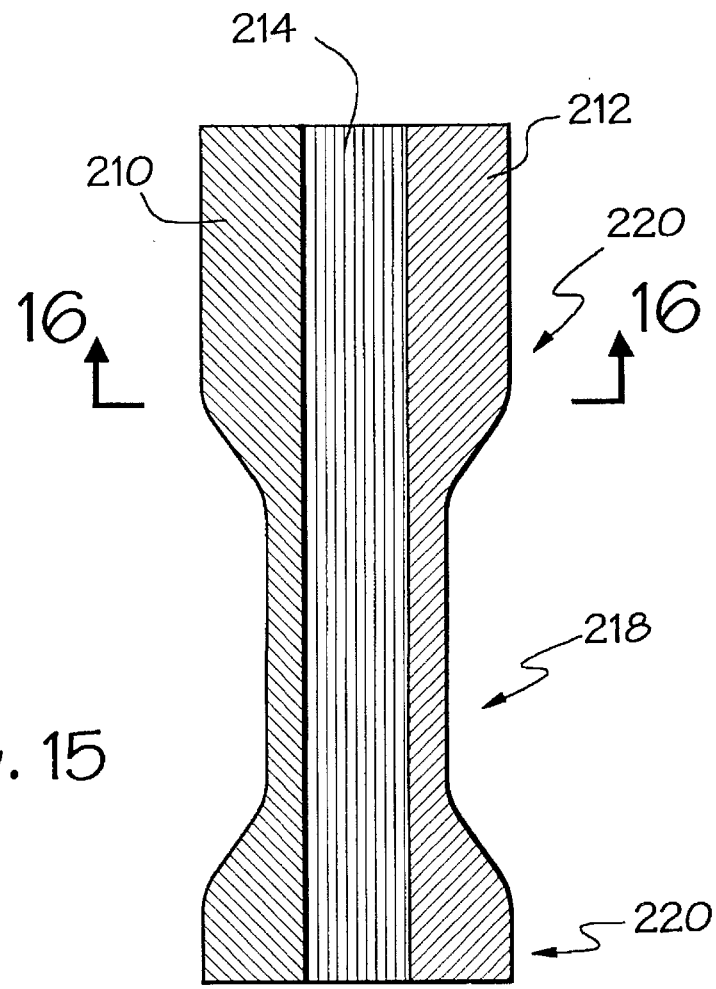
FIG. 15 is a top plan view illustrating an absorbent core structure in accordance with another aspect of the first or second embodiment of the invention showing the two trim pieces in a gap format.
Figure 16:
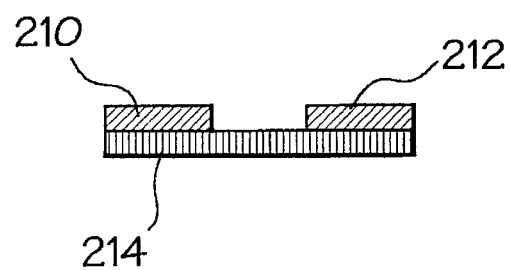
FIG. 16 is a cross-sectional view of the absorbent core structure of FIG. 15 taken along section line 16—16.

As illustrated in FIGS. 13 and 14, the first trim strip 210 and the second trim strip 212 are placed on top of the main pattern strip 214 in an abutting configuration to provide a core structure 216 having two layers of absorbent material in the crotch portion 218 and two layers of absorbent material in the "ears" 220. As a further configuration of this aspect of the invention, the first trim piece 210 and the second trim piece 212 are in a parallel plane but are space apart rather than abutting against each other. This configuration is shown in FIGS. 15 and 16.

Figure 17:
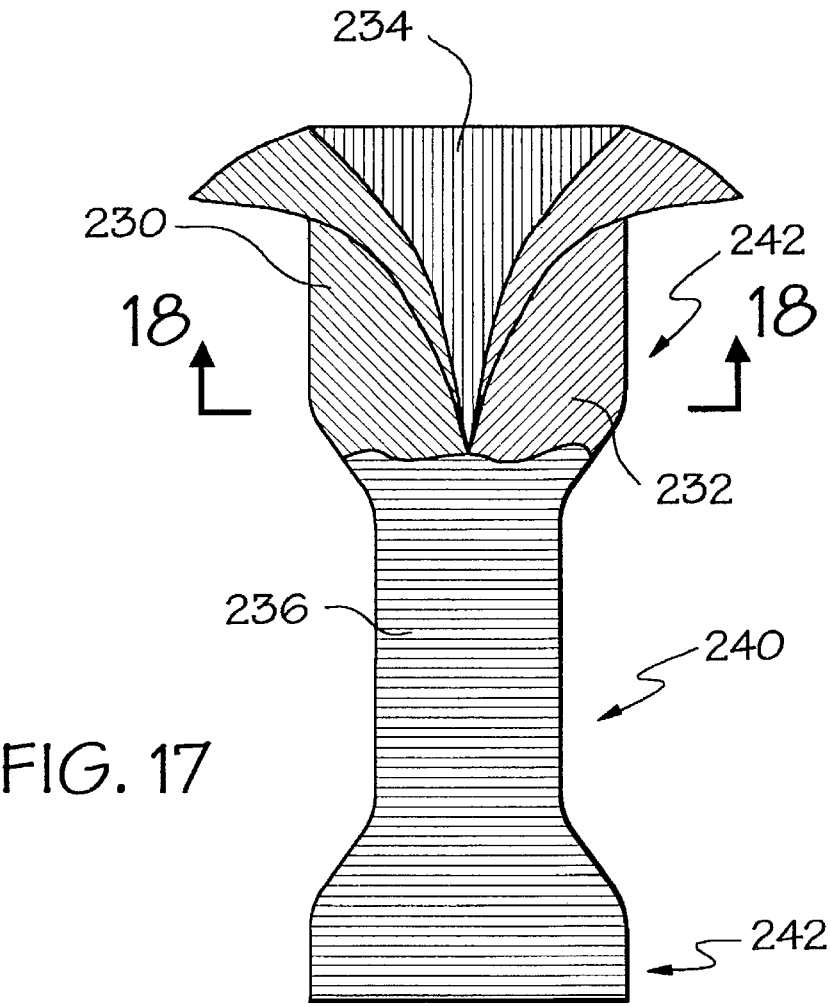
FIG. 17 is a top plan view of an absorbent core structure in accordance with another aspect of the first or second embodiment of the invention showing a first web cutout partially cut away to reveal two trim pieces in butt format partially peeled away to further reveal a second main center web.
Figure 18:
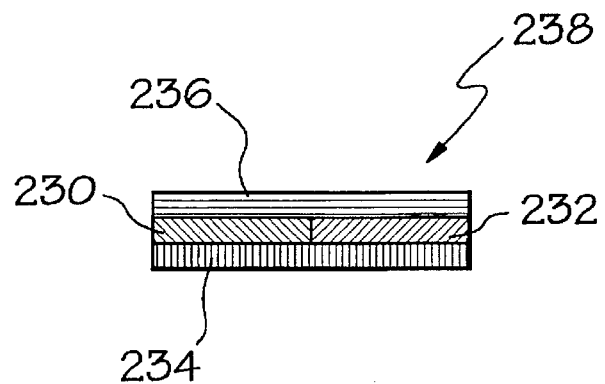
FIG. 18 is a cross-sectional view of the absorbent core structure of FIG. 17 taken along section line 18—18.
Figure 19:
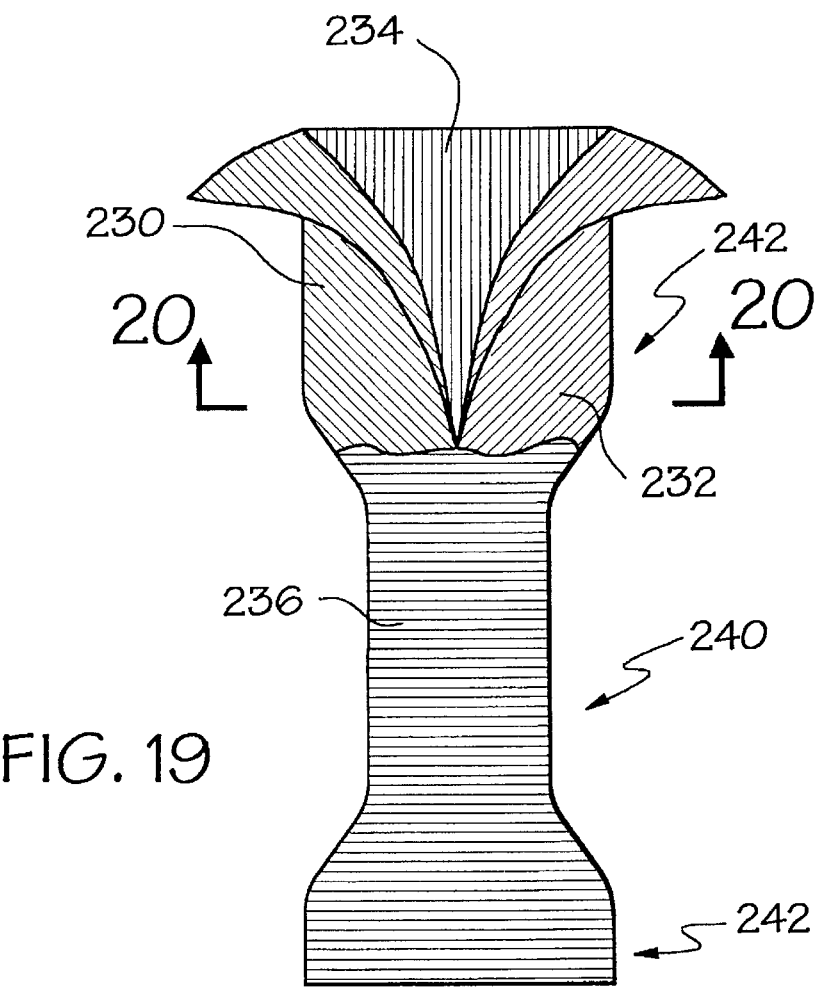
FIG. 19 is a top-plan view of an absorbent core structure in accordance with another aspect of the first or second a third embodiment of the invention showing a first web cutout partially cut away to reveal two trim pieces in gap format partially peeled away to further reveal a second main center web.
Figure 20:
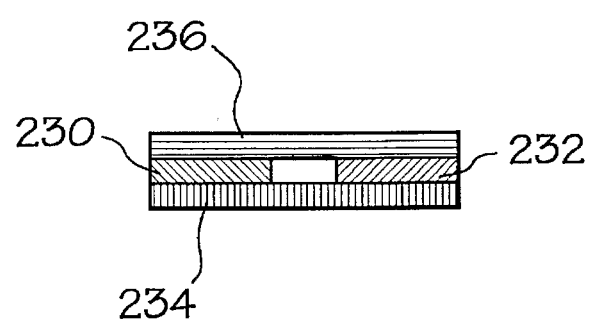
FIG. 20 is a cross sectional view of the absorbent core structure of FIG. 19 taken along section line 20—20.
Figure 21:
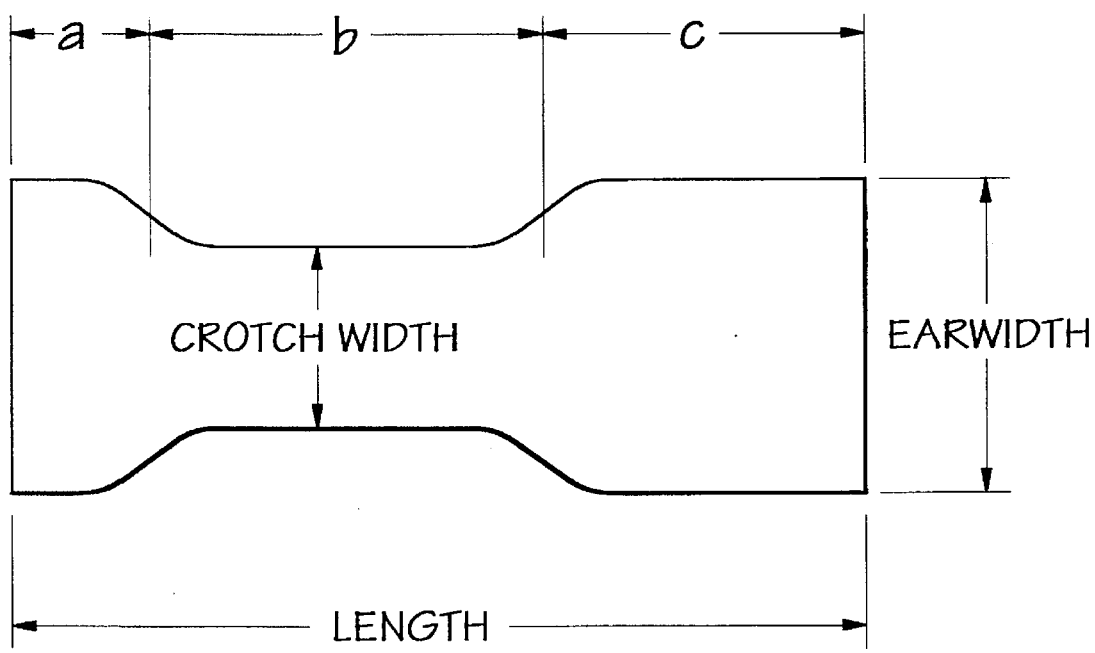
FIG. 21 is a top plan view of a cut-out pattern illustrating the relative shape and dimensions of an absorbent core of the present invention.

In another embodiment of the invention as illustrated in FIGS. 17 and 18, the first trim piece 230 and the second trim piece 232 are placed on top of the full pattern strip 234 in an abutting configuration in the same way that the trim pieces are placed on the full pattern strip illustrated in FIGS. 13 and 14. In this embodiment, however, a second full pattern strip 236 is laid on top of the two trim pieces 230, 232 so that the trim pieces are sandwiched between the first main pattern cutout 234 and the second main pattern cutout 236. As seen in FIG. 18, the resulting core structure 238 has three layers of absorbent material in the crotch portion 240 of the structure and three layers of absorbent material in the "ears" 242. As a further configuration of the third embodiment of the invention, the first trim piece 230 and the second trim piece 232 are in a parallel plane but are spaced apart rather than abutted against each other resulting in the formation of two layers in the central crotch region and three layers in the ear regions. This configuration is illustrated in FIGS. 19 and 20.

While particular embodiments of the present invention have been illustrated and described, it would be obvious to those skilled in the art that various other changes and modifications can be made without departing from the spirit and scope of the invention.

While the multiple configurations of the embodiments of the invention are particularly illustrated in FIGS. 1–20, it will be apparent to those skilled in the art that other configurations are possible. For example, in FIGS. 9–16, the first and second trim pieces may be placed on either surface of the full pattern strip, or the first and second trim pieces may be placed on opposite surfaces of the full pattern strip. In addition to the configurations illustrated in FIGS. 17–20, both trim pieces may be placed on an outer surface of either full pattern strip or the first trim piece may be placed on the outer surface of one full pattern strip and the second trim piece may be placed on the other full pattern strip. Furthermore, the two trim pieces may be placed on opposite surfaces of one full pattern strip and the other full pattern strip may be placed in a facing relationship with either surface of the first full pattern strip. Obviously, the trim pieces in the above configurations may be in an "overlap", "abut" or "gap" format as previously described. It is therefore intended to cover in the appended claims all such changes and modifications that are within the scope of this invention.

What is claimed is:

1. A method for manufacturing a multiple layer absorbent core having a front ear section, a crotch section and a back ear section, wherein the machine direction length of said crotch section equals the combined machine direction length of said front ear section and said back ear section, said core being suitable for use in an absorbent article, said method comprising:

providing a single web of absorbent core material from a roll, said web having parallel straight longitudinal side edges;

continuously transporting said web of absorbent core material in the machine direction;

continuously cutting said web of absorbent core material longitudinally into web sections comprising at least one full-pattern strip having a repeating hourglass-shape defined by first and second non-linear longitudinal edges, and first and second side trim pieces, each of said side trim pieces having a straight edge defined by one of said parallel straight longitudinal side edges of said web and an opposite non-linear longitudinal edge having a pattern corresponding to one of said non-linear longitudinal edges of said full-pattern strip;

continuously orienting said side trim pieces relative to said full-pattern strip such that said non-linear edge of said first side trim piece is superimposed in registration with said first non-linear edge of said full-pattern strip and said second side trim piece is superimposed in registration with said second non-linear edge of said full pattern strip to form a continuous multiple layer composite strip; and successively cutting said composite strip in the transverse direction at predetermined intervals to form discrete multiple layer absorbent cores.

2. The method of claim 1 wherein said web of absorbent core material subsequent to being cut into said at least one full pattern strip and two side pieces is transported by a plurality of horizontal rolls, each of said rolls having a horizontal axis alternately disposed perpendicular or oblique to the machine direction.

3. The method of claim 2 wherein said plurality of horizontal rolls comprises in succession:

a first horizontal roll having a horizontal axis perpendicular to the machine direction of said web;

a second horizontal roll having a horizontal axis oblique to the machine direction of said web;

a third horizontal roll having a horizontal axis perpendicular to the machine direction of said web;

a fourth horizontal roll having a horizontal axis oblique to the machine direction of said web; and a fifth horizontal roll having a horizontal axis perpendicular to the machine direction of said web, wherein said second and fourth horizontal rolls are elevated with respect to said first, third and fifth horizontal rolls.

4. The method of claim 3 wherein said web sections are transported under said first horizontal roll, and said first side trim piece is transported over said second horizontal roll such that the path of said first side trim piece is perpendicular to the horizontal axis of said second horizontal roll, and under said third horizontal roll such that said first side trim piece is superimposed in registration with said full pattern strip, said full pattern strip and said second side trim piece being transported under said third horizontal roll, and wherein said second side trim piece is transported over said fourth horizontal roll such that the path of said second side trim piece is perpendicular to the horizontal axis of said fourth horizontal roll and said second side trim piece is further transported under said fifth horizontal roll such that said second side trim piece is superimposed in registration with said full pattern strip, said full pattern strip having said first side trim piece superimposed thereon being simultaneously transported under said fifth roll.

5. The method of claim 4 wherein said side trim pieces are placed in registration with said full-pattern strip such that said side trim pieces overlap longitudinally in the central portion of said core.

6. The method of claim 4 wherein said side trim pieces are placed in registration with said full-pattern strip such that said side trim pieces are in the same plane.

7. The method of claim 4 wherein said first side trim piece is twisted 180° prior to or subsequent to being transported over said second horizontal roll.

8. The method of claim 4 wherein said second side trim piece is twisted 180° prior or subsequent to being transported over said fourth horizontal roll.

9. The method of claim 1 wherein said web section contains first and second full-pattern strips each having a repeating hourglass-shape, said first and second full-pattern strips being juxtaposed each other along a common line corresponding to one edge of said hourglass pattern, such that one of said full-pattern strips is in advance of the other full-pattern strip by a half cycle, wherein said side trim pieces are superimposed in registration with one of said full-pattern strips and the other full-pattern strip is superimposed in registration with said side trim pieces to form a continuous multiple layer composite strip containing a full-pattern strip as a top layer, one or more intermediate layers of said side trim pieces, and a full-pattern strip as a bottom layer.

10. The method of claim 9 wherein said side trim pieces are placed in registration with said first full-pattern strip such that said side trim pieces overlap in the crotch section.

11. The method of claim 9 wherein said side trim pieces are placed in registration with said full-pattern strip such that said side trim pieces are in the same plane.

12. The method of claim 1 wherein said absorbent core material is a foamed absorbent material.

13. The method of claim 3 wherein said web sections are transported under said first horizontal roll, and said first side trim piece is twisted 180° and transported over said second horizontal roll such that the path of said first side trim piece is perpendicular to the horizontal axis of said second horizontal roll, and said first side trim piece is further transported under said third horizontal roll wherein the upper surface of said first side trip strip prior to being twisted is superimposed in registration with said full pattern strip, said full pattern strip and said second side strip being transported under said third horizontal, and wherein said second side trim piece is twisted 180° and transported over said fourth horizontal roll such that the path of s aid second side trim piece is perpendicular to the horizontal axis of said fourth horizontal roll, and said second side trim piece is further transported under said fifth horizontal roll wherein the upper surface of said second side trim piece prior to being twisted is superimposed in registration with said full pattern strip, said full pattern strip having said first side trim piece superimposed thereon being simultaneously transported under said fifth roll.

14. The method of claim 1 wherein said superimposed side trim pieces are adhesively bonded to said full-pattern strip.

15. The method of claim 9 wherein said superimposed side trim pieces are adhesively bonded to said first and said second full-pattern strips.

16. The method of claim 1 wherein the length of the from ear section is measured from front edge of the front ear to the midway point through the transition between the front ear section and the crotch section, the length of the crotch section is measured from the midway point of the transition between the from ear section and the crotch section to the midway point of the transition between the crotch section and the rear ear section to the end of the rear ear section; the transition between the ear section and the crotch section being symmetrical.

17. A method for manufacturing a multiple layer absorbent core having a front ear section, a crotch section and a back ear section, wherein the machine direction length of said crotch section equals the combined machine direction length of said front ear section and said back ear section, said core being suitable for use in an absorbent article, said method comprising:

providing a single web of absorbent core material from a roll, said web having parallel straight longitudinal side edges;

continuously transporting said web of absorbent core material in the machine direction;

continuously cutting said web of absorbent core material longitudinally into web sections comprising at least one full-pattern strip having a repeating hourglass-shape defined by first and second non-linear longitudinal edges, and first and second side trim pieces, each of said side trim pieces having a straight edge defined by one of said parallel straight longitudinal side edges of said web and an opposite non-linear longitudinal edge having a pattern corresponding to one of said non-linear longitudinal edges of said full-pattern strip;

continuously orienting said side trim pieces relative to said full-pattern strip such that said non-linear edge of said first side trim piece is superimposed in registration with said first non-linear edge of said full-pattern strip and said second side trim piece is superimposed in registration with said second non-linear edge of said full pattern strip to form a continuous multiple layer composite strip; and successively cutting said composite strip in the transverse direction at predetermined intervals to form discrete multiple layer absorbent cores, wherein said web of absorbent core material subsequent to being cut into said at least one full pattern strip and two side pieces is transported by a plurality of horizontal rolls, each of said rolls having a horizontal axis alternately disposed perpendicular or oblique to the machine direction.

* * * * *

UNITED STATES PATENT AND TRADEMARK OFFICE
CERTIFICATE OF CORRECTION

PATENT NO. : 5,597,437
DATED : January 28, 1997
INVENTOR(S) : Stephen J. Lange et al.

It is certified that error appears in the above-indentified patent and that said Letters Patent is hereby corrected as shown below:

Claim 13, Col. 14, line 34, "s aid" should be --said--.

Claim 16, Col. 14, line 48, "from" should be --front--.

Claim 16, Col. 14, line 53, "from" should be --front--.

Signed and Sealed this

Twenty-ninth Day of April, 1997

Attest:

BRUCE LEHMAN

*Attesting Officer*    Commissioner of Patents and Trademarks